United States Patent
Quine et al.

(10) Patent No.: US 7,060,927 B1
(45) Date of Patent: Jun. 13, 2006

(54) METHOD AND SYSTEM FOR ISOLATING AND TESTING BIOLOGICAL CONTAMINANTS IN MAIL PACKAGES

(75) Inventors: Douglas B. Quine, Bethel, CT (US); Denis J. Stemmle, Stratford, CT (US)

(73) Assignee: Pitney Bowes Inc., Stamford, CT (US)

( * ) Notice: Subject to any disclaimer, the term of this patent is extended or adjusted under 35 U.S.C. 154(b) by 47 days.

(21) Appl. No.: 10/742,106

(22) Filed: Dec. 19, 2003

(51) Int. Cl.
*B07C 5/34* (2006.01)
*B65B 9/02* (2006.01)

(52) U.S. Cl. ............... 209/584; 209/583; 209/900; 193/35 R; 53/450

(58) Field of Classification Search ............... 209/884, 209/900
See application file for complete search history.

(56) References Cited

U.S. PATENT DOCUMENTS

| | | | |
|---|---|---|---|
| 4,069,965 A * | 1/1978 | Maddox, Jr. ............... | 232/19 |
| 5,099,679 A | 3/1992 | Huerlimann et al. ........ | 73/19.06 |
| 5,368,226 A * | 11/1994 | Franceschino ............... | 232/19 |
| 6,324,927 B1 | 12/2001 | Ornath et al. ............ | 73/864.33 |
| 6,740,836 B1 * | 5/2004 | Ryan et al. ............... | 209/584 |
| 6,742,703 B1 * | 6/2004 | Esakov et al. ............... | 232/45 |
| 6,789,727 B1 * | 9/2004 | Felice et al. ............... | 232/44 |
| 2003/0155412 A1 | 8/2003 | Felice et al. ............... | 232/45 |
| 2003/0209595 A1 * | 11/2003 | Felice et al. | |
| 2005/0008533 A1 * | 1/2005 | Avant ............... | 422/28 |

FOREIGN PATENT DOCUMENTS

| | | |
|---|---|---|
| EP | 1366696 A2 | 12/2003 |
| GB | 1067166 | 5/1967 |
| GB | 2303111 A | 2/1997 |
| WO | 03/058207 A2 | 7/2003 |

* cited by examiner

*Primary Examiner*—Eileen D. Lillis
*Assistant Examiner*—Jonathan R Miller
(74) *Attorney, Agent, or Firm*—George M. Macdonald; Steven J. Shapiro; Angelo N. Chaclas

(57) ABSTRACT

A method and system for encapsulating mail containers delivered to a building so as to prevent possible contaminants in the mail containers from contaminating the building. An opening is provided on a building wall that substantially separates indoor air circulation from the outdoor air for receiving the mail containers. A plastic tube having a closed end and an open end is used to encapsulate the mail containers. The open end is securely attached to the opening in the wall for receiving the mail containers into the tube, while preventing air circulation outside the building from entering the opening. A sealing device is used to seal the plastic tube for keeping the mail containers in separate sealed sections. A severing device is used to separate the sealed sections in the encapsulated packages so that the encapsulated packages can be tested for the possible contaminants.

15 Claims, 8 Drawing Sheets

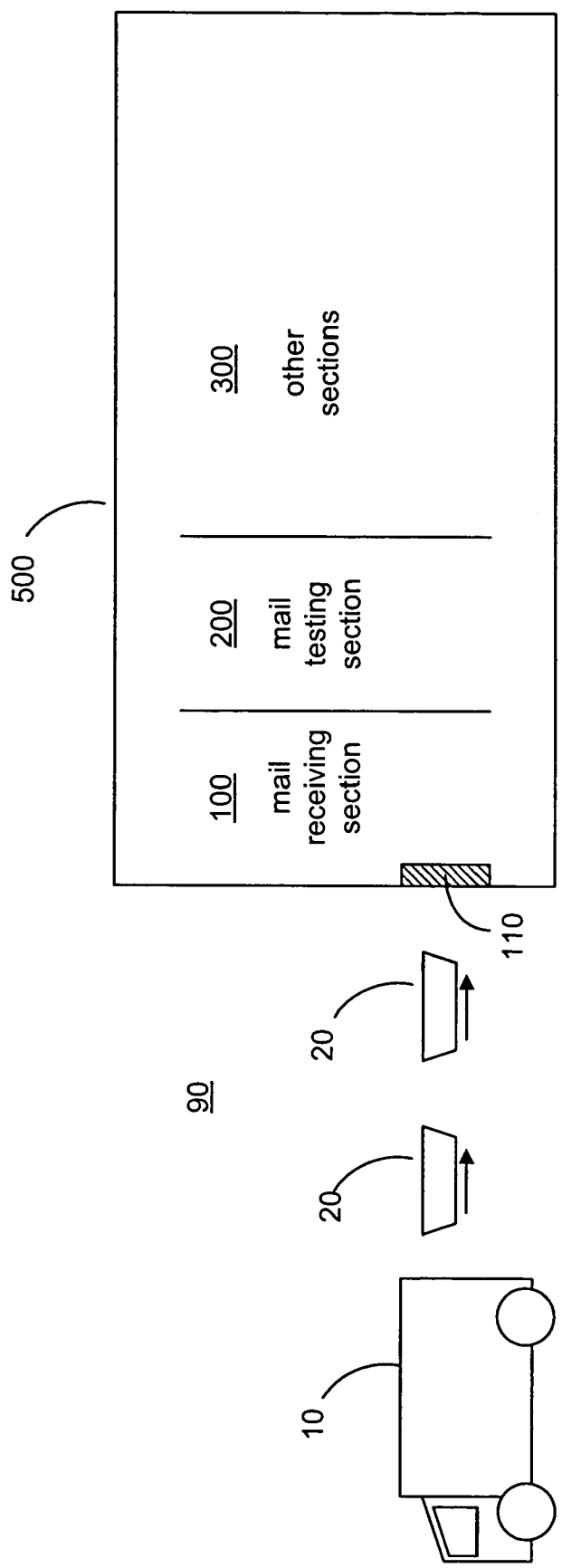

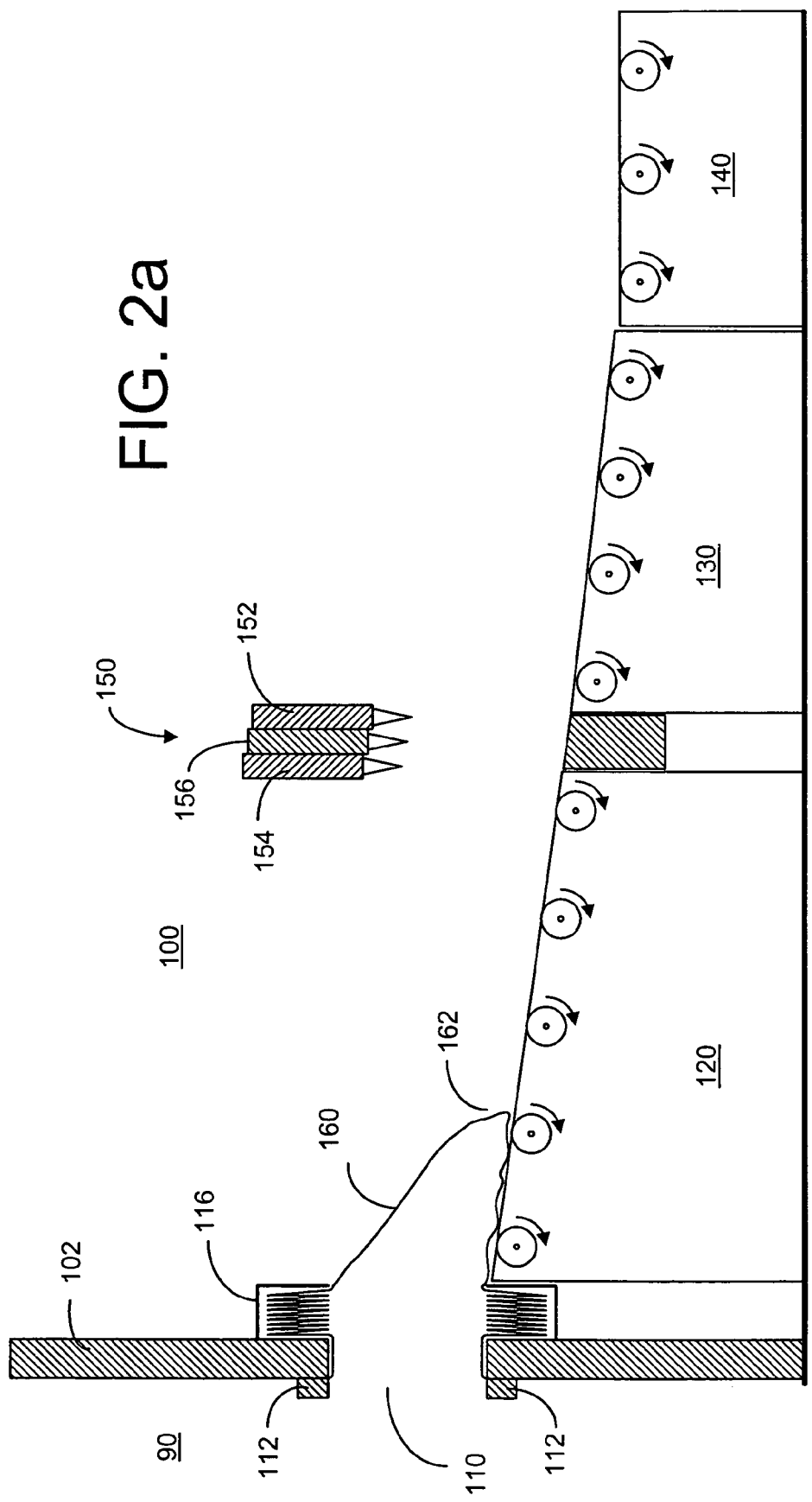

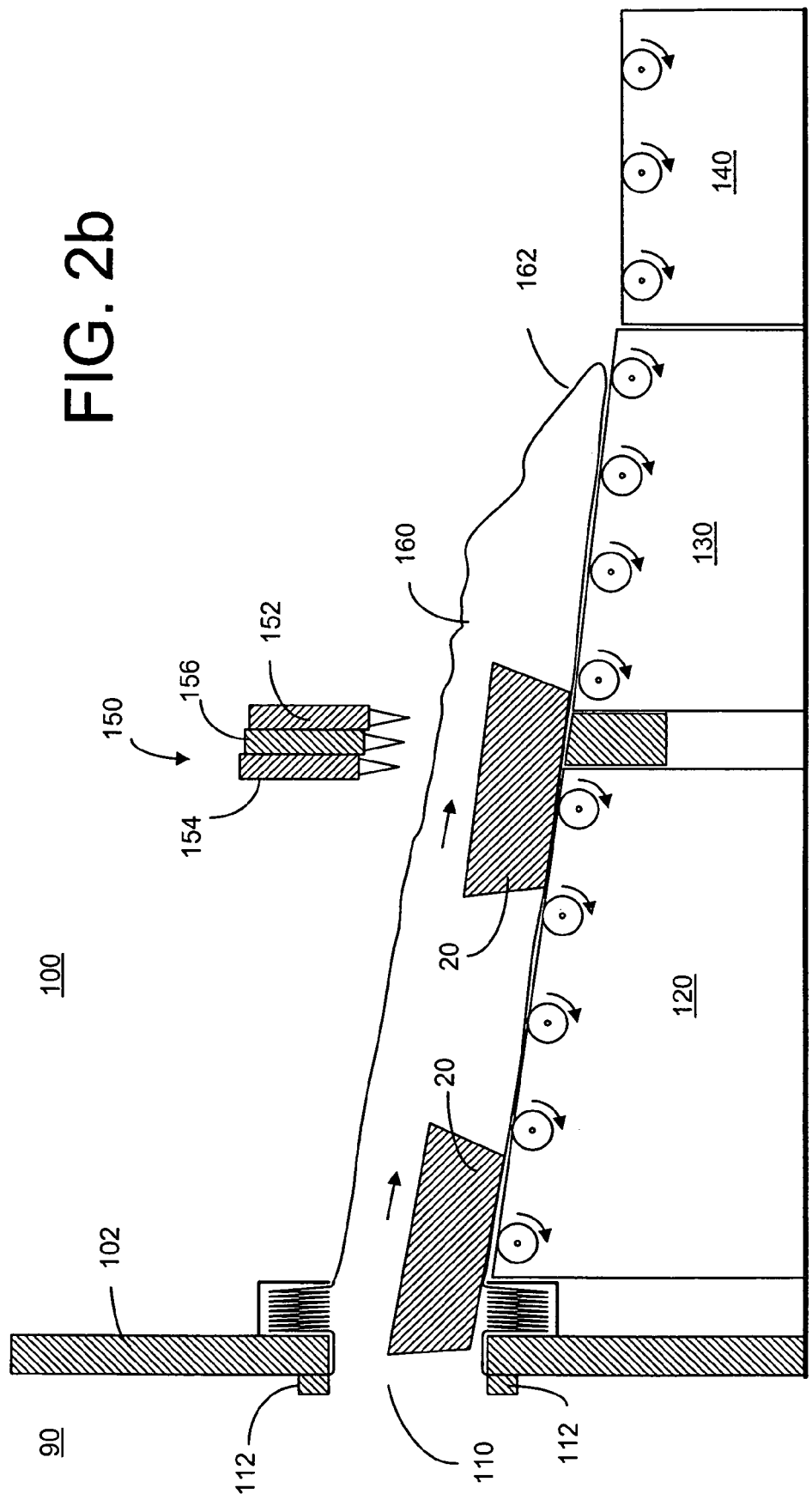

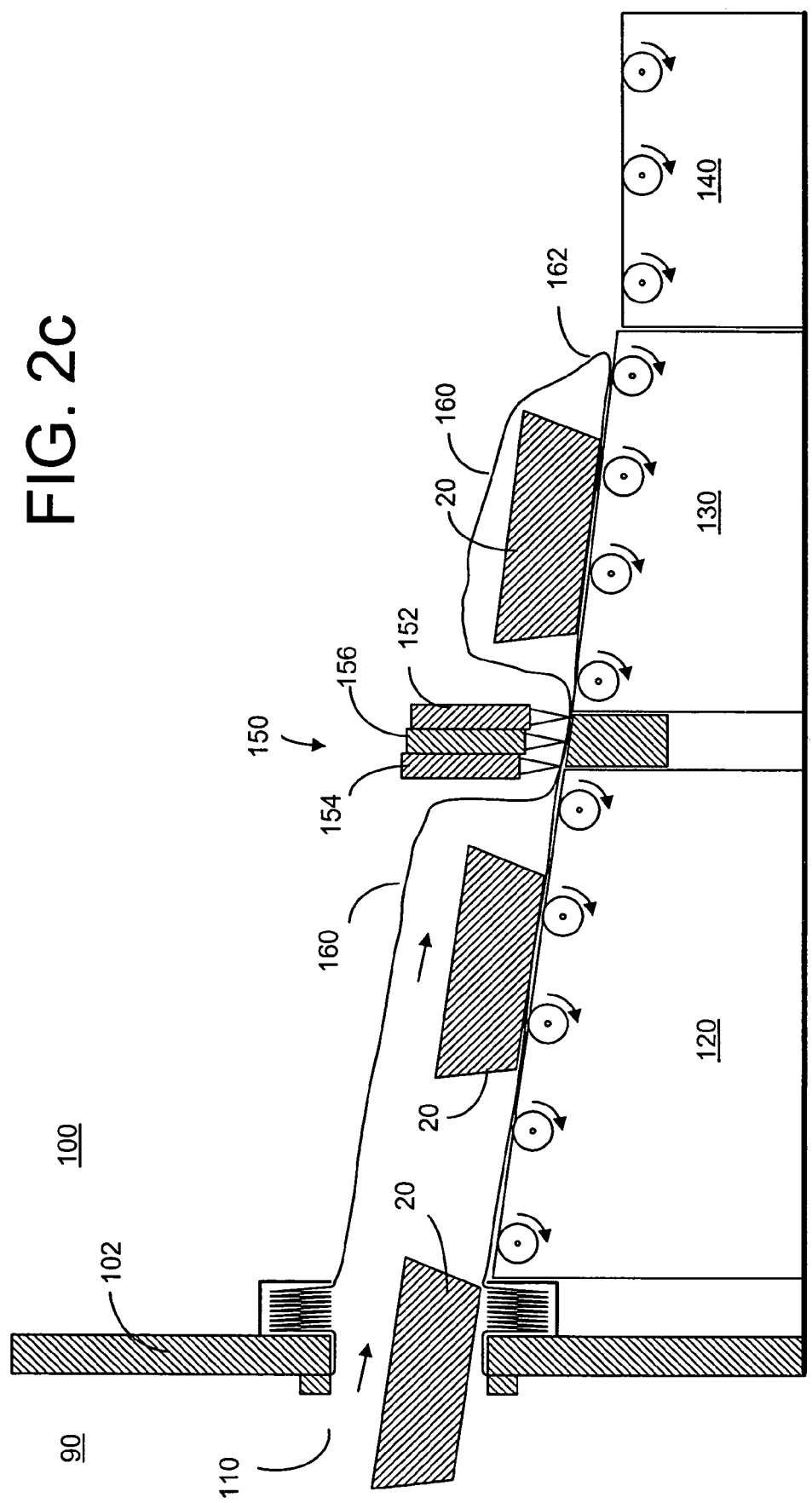

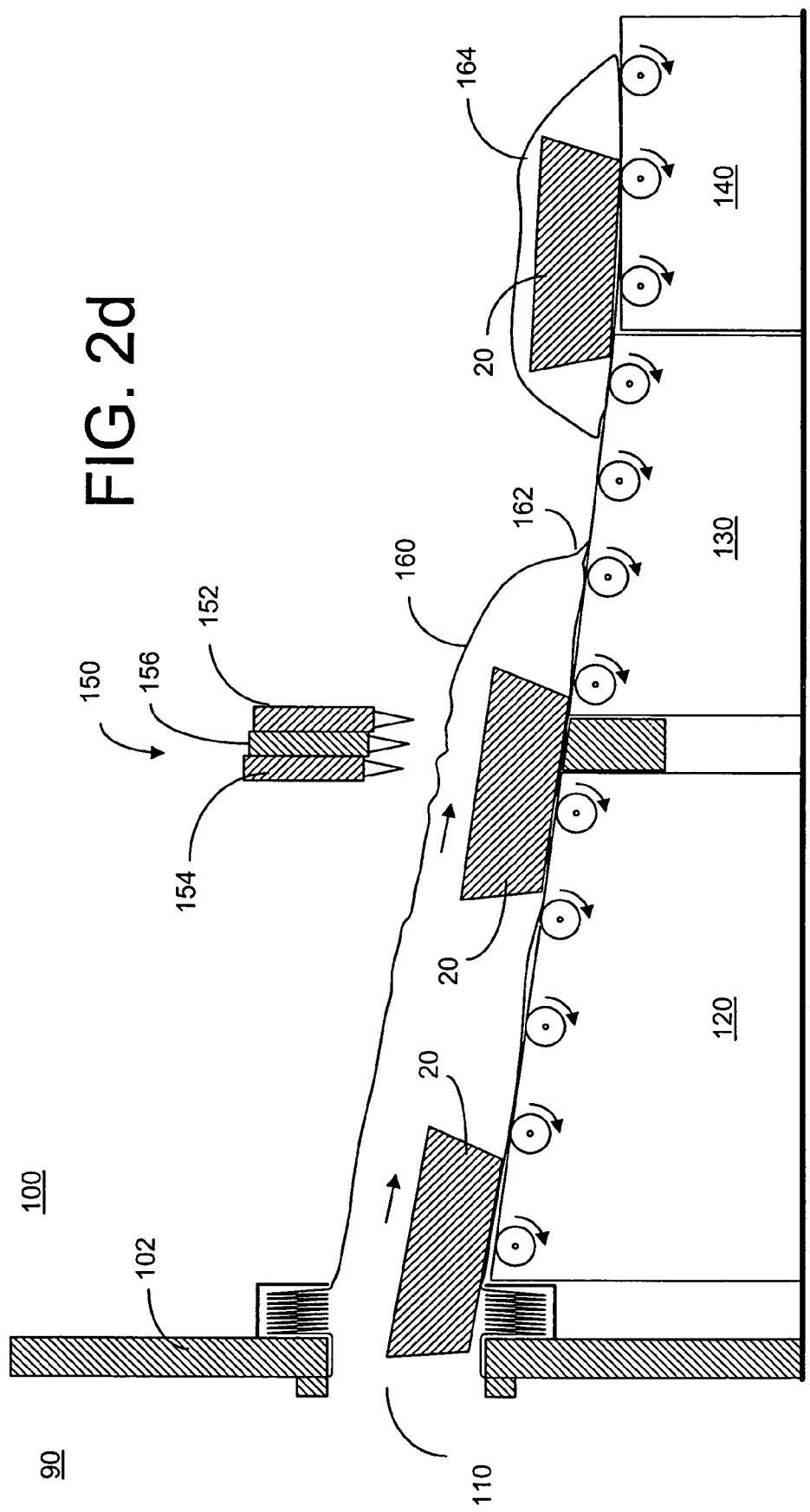

METHOD AND SYSTEM FOR ISOLATING AND TESTING BIOLOGICAL CONTAMINANTS IN MAIL PACKAGES

RELATED APPLICATIONS

The present application is related to commonly owned, co-pending U.S. patent application entitled "Method And Device For Collecting And Transferring Biohazard Samples" (Ser. No. 10/741,264) in the names of Douglas B. Quine, Ashwani Sharma, and John E. Massucci which is hereby incorporated by reference.

The present application is related to commonly owned, co-pending U.S. patent application entitled "Method And Device For Isolating, Collecting And Transferring Biohazard Samples" (Ser. No. 10/742,476) in the names of Douglas B. Quine, Denis J. Stemmle, John E. Massucci, and Deborra J. Zukowski, which is hereby incorporated by reference.

FIELD OF THE INVENTION

The present invention relates generally to biohazard detection and, more particularly, to the isolation of unknown mail in a building for safety testing.

BACKGROUND OF THE INVENTION

In late 2001, several United States postal offices and other buildings were contaminated with *Bacillus anthracis* spores (anthrax) along the Eastern United States, resulting in anthrax infection and death among several individuals. This incident was quite costly, not only in terms of the health-related impact, but also in the required decontamination efforts. Cleanup following the anthrax contamination proved to be difficult, labor intensive, and expensive. As this threat still exists, there exists a need to contain biological contaminants within the postal packages or other containers when the postal packages are delivered to a building suspected to be a target of contamination.

It is advantageous and desirable to provide a method and system for sealing the container in a safe and cost effective way so that the sealed container can be tested for contaminants.

SUMMARY OF THE INVENTION

The present invention provides a method and system for isolating unknown incoming mail from the circulating air of a building. When a mail tray or a postal package is delivered, the mail tray or postal package is sealed in a controlled environment such that the exterior of the sealed package is not contaminated by the contaminants in the mail tray itself. The mail tray is maintained in a sealed condition within the building until it has been fully tested for any hazardous or suspicious materials. The sealed package can be transported within the building without the risk of contaminating the circulating air in the building, without the need for expensive negative pressure isolation chambers, and without the need to implement expensive decontamination procedures in the event that hazardous materials are discovered in the mail. Furthermore, the sealed package can be tested for biological contaminants without exposing the test operators to the mail.

BRIEF DESCRIPTION OF THE DRAWINGS

FIG. 1 is a schematic representation illustrating a general arrangement in a building for receiving mail.

FIG. 2a is a schematic representation illustrating a mail receiving facility having a flexible packaging material for encapsulating incoming mail trays.

FIG. 2b is a schematic representation illustrating a plurality of mail trays being put into the flexible packaging material.

FIG. 2c is a schematic representation illustrating one of the mail trays is being encapsulated.

FIG. 2d is a schematic representation illustrating an encapsulated mail tray being separated from the receiving facility.

DETAILED DESCRIPTION OF THE INVENTION

Figure 3:
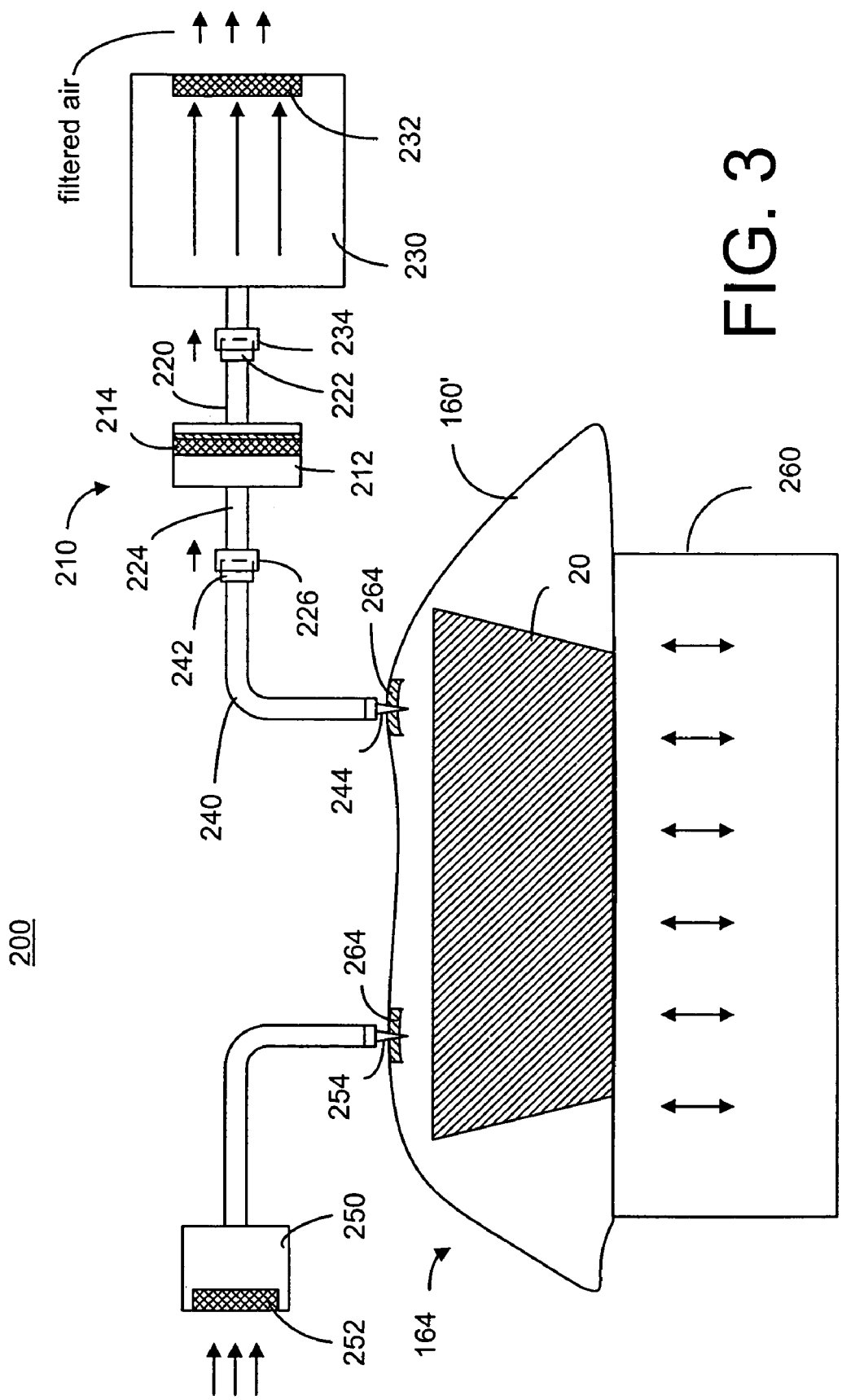
FIG. 3 is a schematic representation illustrating one embodiment of the contaminant testing system.

FIG. 1 is a schematic representation showing the general arrangement for receiving incoming mail into a building 500. As shown in the figure, a special mail-receiving window 110 is used for receiving the mail trays 20 from a mail truck 10. Conveniently, the building 500 can be divided into a mail receiving area 100, a mail testing area 200 and other sections 300. The mail receiving window is designed such that the circulating air within the mail receiving area 100 is substantially isolated from the potential contaminants in the mail trays 20 and the air surrounding the mail trays 20 in the outdoor area 90, it is not necessary to physically separate the mail receiving area 100 from other parts of the building 500. Likewise, the risk of contaminating the mail testing area is also very low. It is not necessary to physically separate the mail testing area with other parts of the building 500.

As shown in FIGS. 2a–2d, the window 110 is simply an opening in an outside wall 102 of the building. Ideally this location is remote from doorways, ventilating air intakes, and loading docks which may allow ambient air to be introduced into the building. The opening can be approximately 2 feet by 2 feet (approximately 60 cm×60 cm), for example, to allow introduction of mail trays 20. The opening can be as small as 12"×14" (30.5 cm×35.6 cm) to accommodate all standard USPS mail trays and standard courier mail items. A supply 116 of flexible encapsulating material 160 is placed near the opening for encapsulating incoming mail trays 20. The encapsulating material 160 can be a long plastic tube with inner end 162 and is heat-sealed or glued. Surrounding the window or opening 110 is an airtight seal 112 for securely mounting the supply 116. As such, the plastic tube 160 creates an airtight barrier separating the air in the mail receiving area 100 and the air in the outdoor area 90. As shown in FIG. 2b, before the mail trays are conveyed into the mail receiving area 100, the plastic tube 160 is pulled out so as to allow one or more mail trays to be introduced into the plastic tube 160. As a mail tray is introduced into the plastic tube 160, it is surrounded on the leading end and the full length of the tray by the encapsulating material. A ramp or conveyer belt 120 is used to support the trays and move them away from the window. As the mail tray slides down the ramp or conveyor belt 120 into an encapsulating station 130, as shown in FIG. 2c, an encapsulating device 150 is used to seal the mail tray in a sealed package and separate the sealed package from the rest of the plastic tube. For example, the encapsulating device 150 comprises two heat sealing devices 152, 154 and a cutting blade 156. The heat sealing device 152 seals the trailing edge of the plastic tube section on the encapsulating station 130 while the heat sealing device 154 creates a new sealed end 162. When the sealing is completed, the cutting blade 156 cuts the plastic tube to allow separation of the encapsulated package 164 from the other mail trays. The encapsulated package 164, as shown in FIG. 2d, can be independently moved to another station 140. The mail tray 20 in the package 164 is now hermetically encapsulated within the plastic tube. Any contaminants in the encapsulated mail tray will remain within the plastic tube, leaving a clean surface on the outside. These packages 164 of encapsulated mail are now safe to move to the mail room for inspection or to the mail testing area 200 for biohazard testing before they are deemed safe for opening within the building 500.

It is advantageous to use a clear plastic for encapsulation. The clear plastic will allow casual observation of powders or foreign materials within the encapsulated package 164 that may be stirred up by shaking or flexing of the mail tray 20 as the package 164 is moved about. Electrostatic treatment of the plastic material (or application of adhesive materials on the inside) may augment the ability to attract such dust or powders. However, using electrostatic plastic materials or adhesive materials may reduce the chance of detecting the potential biohazard in the package because the number of airborne particles is reduced. Thus, it may be more desirable to use transparent, anti-static material for encapsulation. These encapsulated packages 164 may be moved anywhere within the building without the need to move the mailroom to the periphery of the building, without the need to make major changes in the ventilating system to allow isolated air circulation to the mail room, and without the need for negative air pressure chambers and employees in restrictive biological suits and respirators, for example.

Once the mail arrives in the mailroom or the mail testing area 200, it may be tested using any of the mail hazard detection technologies. However, it is advantageous to operatively connect the encapsulated package 164 to a particle collection assembly 210 as shown in FIG. 3. As shown in the figure, the particle collection assembly 210 comprises a filter chamber 212 having a filter 214 for collecting particles that may be biological contaminants in the mail tray 20. On one end of the filter chamber 212, a coupler 222 is provided on a passageway 220. On the other end of the filter chamber 212, another coupler 226 is provided on a passageway 224. The coupler 226 is connected to a tube 240 via a coupler 242. The coupler 222 is connected to an air pump system 232 via coupler 234 so as to draw air through the passageway 224, the filter 214 and the passageway 220. The couplers 222, 226, 234 and 242 are self-sealing polarized (male/female) connectors. A self-seal pad, such as a septum 264, is provided on the encapsulated package 164 so as to allow a needle 244 to puncture through the septum and the encapsulating bag 160' in order to draw an air sample from inside the encapsulated package 164. The self-seal pads may be manufactured in the original plastic tube at intervals of 9 inches, for example, or they may be self adhesive pads that are applied in advance of the needles 244, 254 being introduced to draw an air sample. For providing an additional safety measure, an air filter 232, such a HEPA filter, is used to filter the air drawn by the air pump system 230. Optionally, another self-seal pad 264 is also provided on the encapsulated package 164 so as to provide filtered air to the encapsulated package 164 while the air sample is taken through the particle collection assembly 210. As shown, the filtered air supplying components include an air cleaning filter 252 disposed in a holder 250, operatively connected to a needle 254. When the needles 244, 254 are disconnected from the encapsulated package 164, the self-seal pads 264 prevent the air inside the encapsulated package 164 from escaping to the outside. Advantageously, the encapsulated package 164 is placed on a jogger 260 so that the mail tray 20 can be shaken or flexed in order to stir up the particles in the mail tray for increasing the particle collection efficiency.

Figure 4:
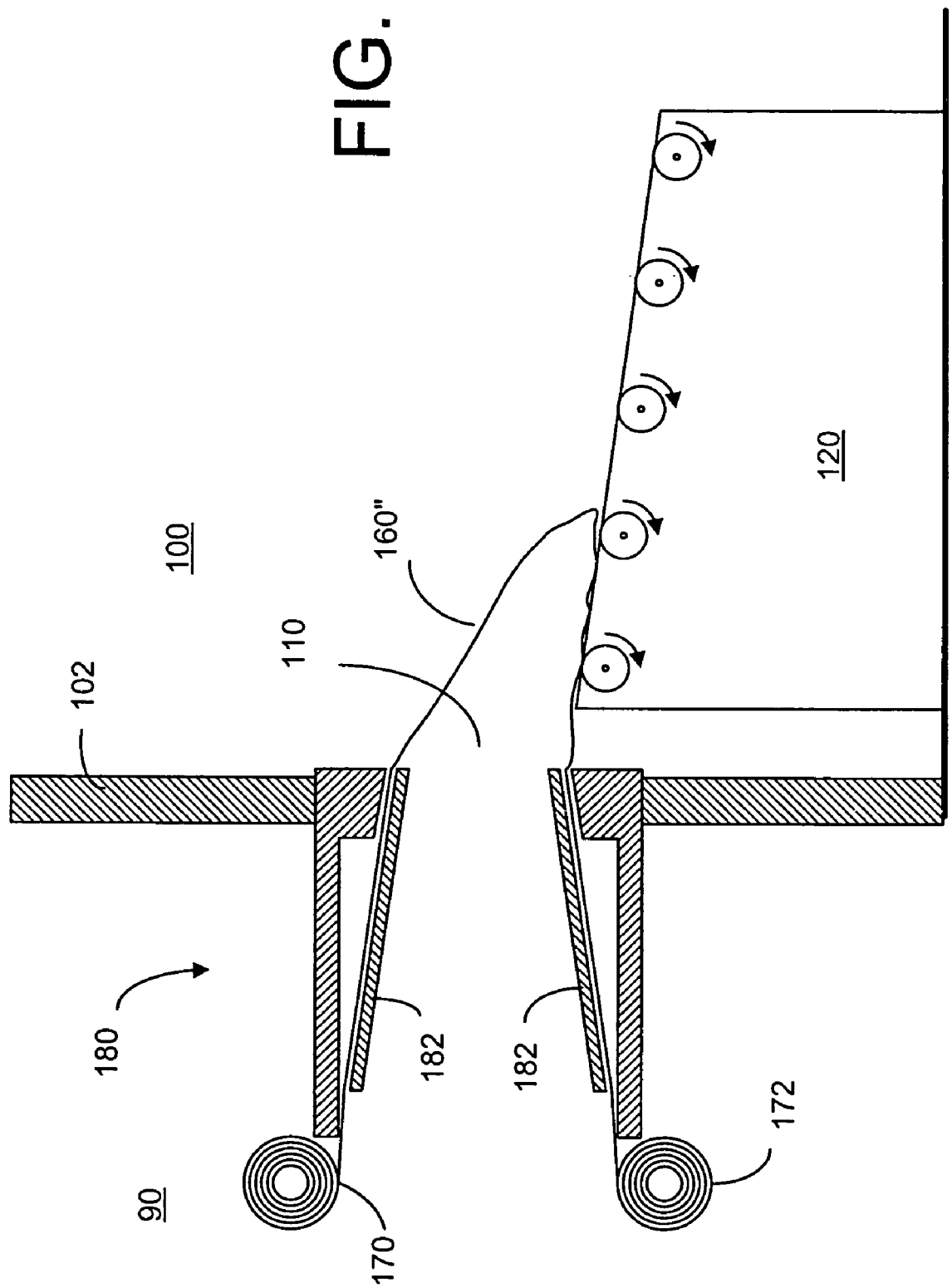
FIG. 4 is a schematic representation illustrating an alternative embodiment of the present invention.
Figure 5:
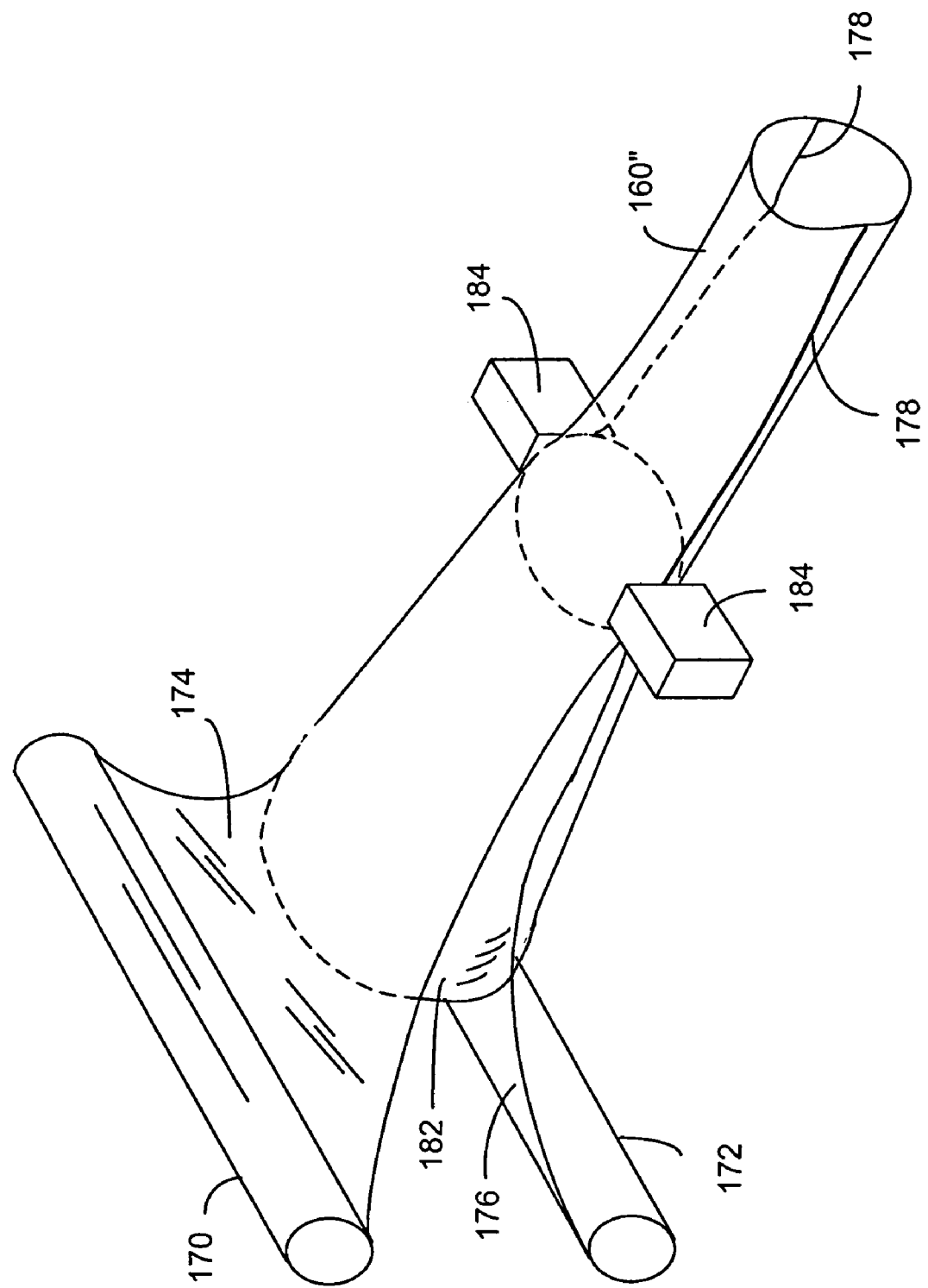
FIG. 5 is a schematic representation illustrating a plastic tube made from two separate plastic sheets.

It should be noted that the plastic tube 160 can also be made from one or more plastic sheets in a sheet-sealing compartment 180 near the opening 110, as shown in FIGS. 4 and 5. As shown in the figures, two rollers 170, 172 of plastic sheet are placed at the sheet-sealing compartment 180 to provide a first plastic sheet 174 and a second plastic sheet 176. The sheets 174, 176 are guided by a conical tube 182 such that the side edges of the sheets meet at a sealing station 184 where the sheets are heat-sealed or glued into a tube 160". The sheets can also be sealed into a tube using ultrasonic, pressure welding or any other technique. As shown in FIG. 5, the tube 160" has two sealed seams 178. It should be understood that the tube 160" can be made from a roller of plastic sheet such that the tube 160" has only one sealed seam 178, but it can also be made from more than two rollers of plastic sheet.

Although the invention has been described with respect to a preferred embodiment thereof, it will be understood by those skilled in the art that the foregoing and various other changes, omissions and deviations in the form and detail thereof may be made without departing from the scope of this invention.

What is claimed is:

1. A method for preventing possible contaminants associated with mailpieces that are to be delivered to a building from contaminating an enclosed space of the building, wherein the enclosed space is defined by at least one wall that separates this enclosed space from an area outside the building, said method comprising:
   providing an opening in the at least one wall for receiving the mailpieces;
   providing a packaging tube having a closed end and an open end, the open end securely attached to the opening so as to prevent air circulation outside the building from entering the enclosed space from the opening;
   receiving the mailpieces into the packaging tube through the open end of the packaging tube; and
   hermetically sealing the packaging tube for encapsulating the mailpieces in at least one sealed tube section;
severing the sealed tube sections into separate encapsulated packages; and
transporting the separate encapsulated packages along a conveyor
   extracting an air sample from each of the encapsulating packages through a filter for collecting on the filter particles that may be contaminants associated with the mailpiece so as to detect the possible contaminants based on the collected particles and wherein the mailpieces are delivered in separate groups and wherein said sealing is carried out for sealing the packing tube at intervals in order to separately encapsulate the groups of the mailpieces in a plurality of sealed tube sections.

2. The method of claim 1, further comprising
   inspecting the sealed tube sections for detecting the possible contaminants.

3. The method of claim 1, further comprising
extracting an air sample through a self-seal pad using a needle from at least one of the sealed tube sections for detecting the possible contaminants.

4. The method of claim 1, further comprising
agitating the encapsulating packages prior to said extracting so as to stir up the particles associated with the mailpieces into the air sample.

5. The method of claim 4, wherein each group of the mailpieces is delivered in a mail container, and wherein said agitating is carried out by disturbing the mail container in the encapsulating package.

6. The method of claim 1, wherein said sealing is carried out by applying heat and pressure to the package tube in a heat-sealing process.

7. The method of claim 1, wherein said sealing is carried out by using an adhesive.

8. The method of claim 1, wherein said sealing is carried out by using an ultrasonic sealing process.

9. The method of claim 1, further comprising
puncturing the mailpieces prior to said extracting for providing an opening in the mailpieces so as to allow the particles associated with the mailpieces to move into the air sample through the opening of the mailpieces.

10. A system for preventing possible contaminants associated with mailpieces that are to be delivered to a building from contaminating an enclosed space of the building, wherein the enclosed space is defined by at least one wall that separates this enclosed space from an area outside the building, and wherein the at least one wall has an opening for receiving the mailpieces, said system comprising:
a packaging tube disposed at the opening, the packing tube having an open end for receiving the mail into the package tube through the open end, the packing tube further having a closed end substantially opposing the open end, wherein the open end is securely attached to the opening so as to prevent air circulation outside the building from entering the enclosed space through the opening;
a sealing device, disposed in the enclosed space in relation to the opening, for hermetically sealing the packaging tube in order to encapsulate the received mailpieces in one or more sealed tube sections;
an air sample extracting device including,
a puncturing device for reaching the air inside said one or more sealed tube sections; and
an air moving device, for moving a sample of the air inside said one or more sealed tube sections to a detector for detecting the possible contaminants associated with the mailpieces;
a filter assembly for collecting in the filter assembly particles that may be contaminants so as to allow said detecting based on the collected particles; and
an agitating device, disposed in relation to said one or more sealed tube sections, for disturbing the mailpieces in the sealed tube sections in order to stir up particles associated with the mailpieces into the air sample,
wherein the mailpieces are delivered in mail containers, said agitating device comprising a jogger disposed below the sealed tube sections for disturbing the mail containers.

11. The system of claim 10, further comprising
a severing device for physically separating the sealed tube sections into a plurality of encapsulated packages so as to allow the encapsulated packages to be tested separately for detecting the possible contaminants.

12. A system for preventing possible contaminants associated with mailpieces that are to be delivered to a building from contaminating an enclosed space of the building, wherein the enclosed space is defined by at least one wall that separates this enclosed space from an area outside the building, and wherein the at least one wall has an opening for receiving the mailpieces, said system comprising:
a packaging tube disposed at the opening, the packing tube having an open end for receiving the mail into the package tube through the open end, the packing tube further having a closed end substantially opposing the open end, wherein the open end is securely attached to the opening so as to prevent air circulation outside the building from entering the enclosed space through the opening;
a sealing device, disposed in the enclosed space in relation to the opening, for hermetically sealing the packaging tube in order to encapsulate the received mailpieces in one or more sealed tube sections;
an air sample extracting device including,
a puncturing device for reaching the air inside said one or more sealed tube sections; and
an air moving device, for moving a sample of the air inside said one or more sealed tube sections to a detector for detecting the possible contaminants associated with the mailpieces; and
a severing device for physically separating the sealed tube sections into a plurality of encapsulated packages, so as to allow the air sample extracting device to separately move the air inside each of the encapsulated packages for detecting the possible contaminants in the mailpieces.

13. The system of claim 12, wherein the packaging tube is made of a substantially clear material so as to allow inspection of the sealed tube sections for detecting the possible contaminants.

14. The system of claim 12, wherein the packaging tube is made of a material that attracts particles that may be contaminants associated with the mailpieces so as to allow the inspection based on the attracted particles.

15. The system of claim 12, wherein each sealed section has at least one septum disposed thereon so as to allow the puncturing device to puncture the septum in order to reach air inside said sealed section.

* * * * *